United States Patent
Sumitran-Holgersson

(10) Patent No.: US 8,173,372 B2
(45) Date of Patent: May 8, 2012

(54) METHODS OF DONOR SPECIFIC CROSSMATCHING

(75) Inventor: Suchitra Sumitran-Holgersson, Stockholm (SE)

(73) Assignee: AbSorber AB, Stockholm (SE)

( * ) Notice: Subject to any disclaimer, the term of this patent is extended or adjusted under 35 U.S.C. 154(b) by 0 days.

(21) Appl. No.: 10/439,666

(22) Filed: May 16, 2003

(65) Prior Publication Data

US 2003/0228638 A1   Dec. 11, 2003

Related U.S. Application Data

(60) Provisional application No. 60/381,033, filed on May 16, 2002.

(51) Int. Cl.
  *G01N 33/53* (2006.01)
  *G01N 33/543* (2006.01)
(52) U.S. Cl. ........ 435/7.1; 435/7.2; 435/7.21; 435/7.23; 435/334; 435/344; 435/344.1; 435/371; 435/174; 435/7.92; 436/518; 436/512; 436/64
(58) Field of Classification Search .................... 435/7.1, 435/7.2, 7.21, 7.23, 334, 344, 344.1, 371, 435/174, 7.92; 436/518, 64, 512
See application file for complete search history.

(56) References Cited

U.S. PATENT DOCUMENTS

| | | | |
|---|---|---|---|
| 4,352,883 A | 10/1982 | Lim | |
| 4,353,888 A | 10/1982 | Sefton | |
| 4,654,267 A | 3/1987 | Ugelstad et al. | |
| 4,714,680 A * | 12/1987 | Civin | 435/347 |
| 4,965,204 A | 10/1990 | Civin | |
| 4,968,733 A | 11/1990 | Müller et al. | |
| 4,976,859 A | 12/1990 | Wechs | |
| 5,026,365 A | 6/1991 | Rossini et al. | |
| 5,035,994 A | 7/1991 | Civin | |
| 5,071,741 A | 12/1991 | Brockbank | |
| 5,084,350 A | 1/1992 | Chang et al. | |
| 5,130,144 A | 7/1992 | Civin | |
| 5,137,809 A | 8/1992 | Loken et al. | |
| 5,158,881 A | 10/1992 | Aebischer et al. | |
| 5,257,984 A | 11/1993 | Kelley | |
| 5,284,761 A | 2/1994 | Aebischer et al. | |
| 5,482,841 A | 1/1996 | Buelow | |
| 5,518,890 A | 5/1996 | Starkweather et al. | |

(Continued)

FOREIGN PATENT DOCUMENTS

WO   WO 92/04033   3/1992

(Continued)

OTHER PUBLICATIONS

Asahara, T. et al. Isolation of putative progenitor endothelial cells for angiogenesis. Science. 1997;275:964-967.*

(Continued)

*Primary Examiner* — Mark Shibuya
*Assistant Examiner* — Pensee Do
(74) *Attorney, Agent, or Firm* — Mintz Levin Cohn Ferris Glovsky and Popeo, P.C.; Ivor R. Elrifi; Cynthia A. Kozakiewicz

(57) ABSTRACT

The detection of endothelial cell antibodies has been proven clinically important for successful organ transplantation. Disclosed are methods of isolating Tie-2$^+$ and CD34$^-$ precursor endothelial cells for use in donor-specific crossmatching.

5 Claims, 6 Drawing Sheets

U.S. PATENT DOCUMENTS

| | | | |
|---|---|---|---|
| 5,750,397 A | 5/1998 | Tsukamoto et al. | |
| 5,800,828 A | 9/1998 | Dionne et al. | |
| 5,840,502 A * | 11/1998 | Van Vlasselaer | 435/7.21 |
| 5,843,633 A * | 12/1998 | Yin et al. | 435/2 |
| 5,942,385 A * | 8/1999 | Hirth | 435/4 |
| 5,955,291 A * | 9/1999 | Alitalo et al. | 435/7.23 |
| 6,017,719 A * | 1/2000 | Tseng-Law et al. | 435/7.21 |
| 6,287,875 B1 | 9/2001 | Geisberg | |
| 6,309,643 B1 | 10/2001 | Braun et al. | |
| 6,376,653 B1 | 4/2002 | Holmes et al. | |
| 2002/0098166 A1* | 7/2002 | Havemann et al. | 424/93.1 |
| 2003/0100107 A1 | 5/2003 | Peschle | |
| 2003/0148952 A1* | 8/2003 | Crombleholme | 514/12 |
| 2006/0035290 A1* | 2/2006 | Popa et al. | 435/7.21 |

FOREIGN PATENT DOCUMENTS

| | | |
|---|---|---|
| WO | WO 92/19195 | 11/1992 |
| WO | WO 93/14191 | 7/1993 |
| WO | WO 95/05452 | 2/1995 |
| WO | WO 95/07611 | 3/1995 |
| WO | WO 96/27287 | 9/1996 |
| WO | WO 96/29862 | 10/1996 |
| WO | WO 98/14058 | 4/1998 |
| WO | WO 00/24897 | 5/2000 |
| WO | WO 03/014326 A2 | 2/2003 |

OTHER PUBLICATIONS

Peichev, M. et al. Expression of VEGFR-2 and AC133 by circulating human CD34+ cells identifies a population endothelial precursors. Blood. 2000;95:952-958.*
Gehling, U.M. et al. In vitro differentiation of endothelial cells from AC133-positive progenitor cells. Blood. 2000;95:3106-3112.*
To, L.B. et al. The biology and clinical uses of blood stem cells. Blood. 1997;89:2233-2258.*
Holyoake, T.L. The CD34 antigen: Potential clinical advantages of CD34 selection. Clin. Oncol. 1996;8:214-221.*
Siena, S. et al. Flow cytometry for clinical estimation of circulating hematopoietic progenitors for autologous transplantation in cancer patients. Blood. 1991;77:400-409.*
Siena, S. et al. Circulation of CD34+ hematopoietic stem cells in the peripheral blood of high-dose cyclophosphamide-treated patients: Enhancement of intravenous recombinant human granulocyte-macrophage colony-stimulating factor. Blood. 1989;74:1905-1914.*
Civin, C.I. et al. Antigenic analysis of hematopoiesis. III. A hematopoietic progenitor cell surface antigen defined by a monoclonal antibody raised against KG-1a cells. J. Immunol. 1984;133:157-165.*
Osawa, M., et al. Long-term lymphohematopoietic reconstitution by a single CD34-low/negative hematopoietic stem cell. Science. 1996;273:242-245.*
Borg, A.A., Seminars in Arthritis and Rheumatism, 27(3):186-195 (1997).
Brasile, et al., Am. J. Med., 87:74-80 (1989).
Cerilli, et al., Transplantation Proceedings, XIX(4):47-49 (1987).
Dimitriu-Bona, et al., Clin. Immunol. Immunopathol., 76(3)234-240 (1995).
Jones, et al., J. Physiol. Pharmacol., 51(4):813-820 (2000).
International Search Report for PCT/IB03/02502, mailed Apr. 15, 2004.
Drake, et al., Human Reproduction, 6(8):1156-1159 (1991).
George, et al., Thrombosis and Haemostasis, 67(1):147-153 (1992).
Jackson, et al., J. Cell Sci., 96:257-262 (1990).
Joplin, et al., In Vitro Cell. Dev. Biol., 25:1189-1192 (1989).
Matsubara, et al., Current Eye Res., 20(1):1-7 (2000).
Peichev, et al., Blood, 95(3):952-958 (2000).
Perrey, et al., Transplant Immunol., 6:101-106 (1998).
Sbarbati, et al., Blood, 77(4):764-769 (1991).
Vermehren, et al., Transplantation, 72(11):1479-1486 (2002).
Woolf, et al., Pediatr. Nephrol., 16:177-184 (2001).
Invitation to Pay Additional Fees, Mailing date: Dec. 23, 2003.
"Online Data Supplements", Circ. Res., XP-002373138, retrieved from the Internet: URL:http://circres.ahajournals.org/cgi/content/full/01.RES.0000177670.72216.9b/DC1>, Jul. 14, 2005.

Asahara et al., "Isolation of Putative Progenitor Endothelial Cells for Angiogenesis", Science, 275:964-967(1997).
Bhatia et al., "A newly discovered class fo human hematopoietic cells with SCID-repopulating activity", Nat. Med.,49)1038-10454 (1998).
Brasile et al., "The association of antivascular endothelial cell antibody with hyperacute rejection: A case report", Surgery, 99(5):637-640 (1986).
Cerilli et al., "Endothelial Cell Alloantigens", Transplant. Proc., 12(3, Suppl. 1):37-42 (1980).
Cerilli et al., "The Significance of the Monocyte Crossmatch in Recipients of Living-related HLA Identical Kidney Grafts", Human Immunol., 7:45-50 (1983).
Chapman et al., "Immunoglobulin Class and Specificity of Antibodies Causing Postivie T Cell Crossmatches. Relationship to Renal Transplant Outcome", Transplant., 42(6):608-613 (1986).
Elsheikh et al. Only a specific subset of human peripheral-blood Monocytes has endothelial-like functional capacity, Blood, 106(7):2347-2355(2005).
Fan et al., "Dynamic DNA Hybridization on a Chip Using Paramagnetic Beads", Analytical Chemistry, 71:4851-4859 (1999).
Gruber, S.A., "The Case for Local Immunosuppression", Transplant., 54(1): 1-11 (1992).
Hosenpud et al., "Cardiac Allograft Vasculopathy. Association with Cell-Mediated but Not Humoral Alloimmunity to Donor-Specific Vascular Endothelium", Circulation, 92(2):205-211 (1995).
Ianhez et al., "Humoral Rejection with Negative Crossmatches", Transplant. Proceedings, 21(1):720-721 (1989).
Kalil et al., "Humoral Rejection in Two HLA Identical Living Related Donor Kidney Transplants", Transplant. Proceedings, 21(1):711-713 (1989).
Karlsson et al., "Nucleation and Growth of Ice Crystals Inside Cultured Hepatocytes During Freezing in the Presence of Dimethyl Sulfoxide", Biophys. J., 65:2524-2536 (1993).
Kissmeyer-Nielsen et al., "Hyperacute Rejection of Kidney Allografts, Associated with Pre-Existing Humoral Antibodies Against Donor Cells", Lancet, 2(7465):662-665 (1966).
Mohanakumar et al., "Serological Characterization of Antibodies Eluted From Chronically Rejected Human Renal Allografts", Transplant., 32(1):61-66 (1981).
Moraes et al., "Alloantibodies Against Donor Epidermis and Early Kidney Transplant Rejection", Transplant., 51(2):370-373 (1991).
Murohara et al., "Transplanted cord blood-derived endothelial precursor cell augment postnatal neovascularization", J. Clin. Invest., 105(11):1527-1536 (2000).
Nowak et al., "Expression of vascular endothelial growth factor receptor-2 or Tie-2 on peripheral blood cells defines functionally competent cell populations capale of reendothelialization", Circulation, 110(24):3699-3707 (2004).
Paul et al., "Antibodies Against Renal Endothelial Alloantigens", Transplant. Proc., 12(3, Suppl. 1):43-48 (1980).
Pierce et al., "A Mixed Antiglobulin Test With Kidney Cells in Suspension for IgG Antibody in Human Allograft Recipients", Transplant., 19(4):343-348 (1975).
Rehman et al., "Peripheral blood 'endothelial progenitor cedlls' are derived from monocyte/macrophages and secrete angiogenic growth factors", Circulation, 107(8):1164-1169 (2003).
Romagnani et al., CD14+CD34$^{low}$ cells with stem cell phenotypic and functional features are the major source of circulating endothelial progenitors:, Circ. Res., 97(4):314-322 (2005).
Schnürch et al., "Expression of tie-2, a member of a novel family of receptor tyrosine kinases, in the endothelial cell lineage", Development, 119:957-968 (1993).
Smithies et al., "Insertion of DNA sequences into the human chromosomal β-globin locus by homologous recombination", Nature, 317:230-234 (1985).
Stastny, P., "Endothelial-Monocyte Antigens", Transplant. Proceedings, 12(3, Suppl. 1):32-36 (1980).
Sumitran-Holgersson et al., "Identification of the Nonclassical HLA Molecules, MICA, as Targets for Humoral Immunity Associated with Irreversible Rejection of Kidney Allografts", Transplant., 74(2):268-277 (2002).

Sumitran-Karuppan et al., "Fewer Acute Rejection Episodes and Improved Outcome in Kidney-Transplanted Patients with Selection Criteria Based on Crossmatching", *Transplant.*, 53(3):666-673 (1992).

Sumitran-Karuppan et al., "Hyperacute rejections of two consecutive renal allografts and early loss of the third transplant caused by non-HLA antibodies specific for endothelial cells" *Transplant. Immunol.*, 5(4):321-327 (1997).

Sumitran-Karuppan et al., "Specific Inhibition of HLA Class I and II Antibodies by Soluble Antigens—A Method for the Identification of Antibody Specificity in SERA From Alloimmunized Individuals", *Transplant.*, 58(6):713-719 (1994).

Sumitran-Karuppan et al., "The Use of Magnetic Beads Coated with Soluble HLA Class I or Class II Proteins in Antibody Screening and for Specificity Determination of Donor-Reactive Antibodies" *Transplant.*, 61(10):1539-1545 (1996).

Sumitran-Karuppan, S., "The Clinical Importance of Choosing the Right Assay for Detection of HLA-Specific Donor-Reactive Antibodies", *Transplant.*, 68(4):502-509 (1999).

Ting, A., "Postive crossmatches—when is it safe to transplant?" *Transplant.*, 2:2-7 (1989).

Vartdal et al., "HLA class I and II typing using cells positively selected from blood by immunomagnetic isolation—a fast and reliable technique", *Tissue Antigens*, 28(5):301-312 (1986).

Wilson, C.B., "Individual and Strain Differences in Renal Basement Membrane Antigens", *Transplant. Proceedings*, 12(3, Suppl. 1):69-73 (1980).

Yang et al., "Functional Roles for PECAM-1 (CD31) and VE-Cadherin (CD144) in Tube Assembly and Lumen Formation in Three-Dimensional Collagen Gels", *Am. J. Pathol.*, 155(3):887-895 (1999).

Zheng et al., "Fidelity of targeted recombination in human fibroblasts and murine embryonic stem cells", *Proc. Nat'l. Acad. Sci. U.S.A.*, 88:8067-8071 (1991).

* cited by examiner

METHODS OF DONOR SPECIFIC CROSSMATCHING

RELATED APPLICATIONS

This application claims priority to U.S. Ser. No. 60/381,033, filed May 16, 2002, the content of which is incorporated herein by reference in its entirety.

FIELD OF THE INVENTION

The invention relates to a method for the direct isolation of endothelial cells from whole blood for routine donor-specific crossmatching to detect anti-endothelial cell antibodies prior to organ transplantation.

BACKGROUND OF THE INVENTION

The presence of donor lymphocyte-reactive Human Leukocyte Antigen (HLA)-specific antibodies either before and/or after renal allograft transplantation has been associated with hyperacute rejections, early acute rejections, and poor graft survival. However, rejections may occur in the absence of detectable lymphocytotoxic antibodies, suggesting that non-HLA antigenic systems may also play a role in renal allograft hyperacute and acute rejections. Antibodies reactive with endothelial cells and monocytes (also called the EM-antigenic system), or only with endothelial cells, have been described and reported to have a deleterious effect in several organ transplantations.

Recently, the major histocompatibility class I-related chain A antigen (MICA) expressed on endothelial cells was identified as one of the target antigens of humoral immunity associated with irreversible rejections of kidney allografts. Studies of HLA-identical living-related donor allografts showed that the presence of endothelial cell/monocyte reactive antibodies correlated with rejection, graft loss, and poor allograft function. It was reported that this reactivity could be responsible for up to 80% of irreversible rejections in this group of patients. However, the routinely used lymphocyte cross-match (LXM) does not permit detection of the clinically relevant HLA class-I, class-II, endothelial/monocyte-reactive and endothelial cell-specific antibodies. Although the presence of circulating endothelial cells in whole blood has been a subject of debate for many years, the existence of circulating precursor endothelial cells in adult humans has recently been reported by some investigators. However, there is currently no suitable method available to perform a routine donor-specific endothelial cell-crossmatch (ECXM).

Therefore, there is a need to efficiently perform routine donor-specific endothelial cell cross-matching to aid in the identification of better donor-recipient combinations, which will thereby have a greater impact on transplant survival than the current method of lymphocyte cross-match.

SUMMARY OF THE INVENTION

The invention pertains to a method of isolating endothelial cells which are useful in donor specific crossmatching prior to transplantation. The isolated endothelial cells are also useful in diagnosing various vascular and immune related disorders.

The invention includes a method of isolating an endothelial cell from a biological sample by providing a sample known to contain, or suspected of containing, an endothelial cell. The endothelial cell is Tie-2 positive. Alternatively, the isolated endothelial cell is VEGFR positive. The isolated endothelial cell is a mature cell. Alternatively, the isolated endothelial cell is an endothelial cell precursor. The sample is contacted with a detection reagent to form a detection reagent-endothelial cell complex. The endothelial cell is isolated by separating the complex form the sample. Separation is accomplished, for example, by flow cytometry or use of a magnetic field.

The detection reagent is a ligand for an endothelial sell surface receptor such as angiopoietin or vascular endothelial growth factor (VEGF). Alternatively the detection reagent is an antibody specific for an endothelial cell surface receptor such as Tie-2 or the vascular endothelial growth factor receptor (VEGFR). The antibody is an intact antibody or an antibody fragment (e.g. Fab, or Fv). The detection reagent is attached to a solid support, such as a non-magnetic, magnetic, or paramagnetic bead.

The biological sample is whole blood, sera, tissue homogenate, peripheral blood mononuclear cells (PBMCs) or leucapherisate.

The invention further provides a method of cross-matching a donor and a recipient by providing a biological sample from a donor that is known to contain an endothelial cell, contacting the donor sample with detection reagent to isolate an endothelial cell. A recipient biological sample is screened for reactivity with the donor isolated endothelial cell. No reactivity between the recipient sample and the isolated endothelial cell indicates compatibility between the donor and recipient and a higher probability that the organ transplant will be successful.

In a further aspect, the invention includes a method of diagnosing an immune related or vascular disorder in a subject by providing a first sample from a subject known to contain, or suspected of containing, an endothelial cell. The first sample is contacted with a second sample. The second sample is from a subject known to contain, or suspected of containing, an auto antibody. Alternatively the second sample contains reagents (e.g. antibodies) that recognize endothelial cell surface markers associated with the particular disorder. Complex formation between the endothelial cell and the second sample is determined. The presence of the complex indicates the disorder in the subject.

In yet another aspect, the invention includes a method of determining the efficacy of treatment or prognosis of an immune related or vascular disorder in a subject by providing a first sample from a subject known to contain, or suspected of containing, an endothelial cell, contacting the endothelial cell with a second sample from a subject known to contain, or suspected of containing, an autoantibody, measuring any autoantibody-endothelial cell precursor complex present to yield a subject profile. The subject profile is compared with a reference profile, wherein a similarity between the subject profile and reference profile indicates that the treatment is efficacious or a favorable prognosis.

Immune related or vascular disorders include vasculitis, atherosclerosis, bleeding disorders, angiogenesis, thrombosis, defective wound healing, and transplantation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
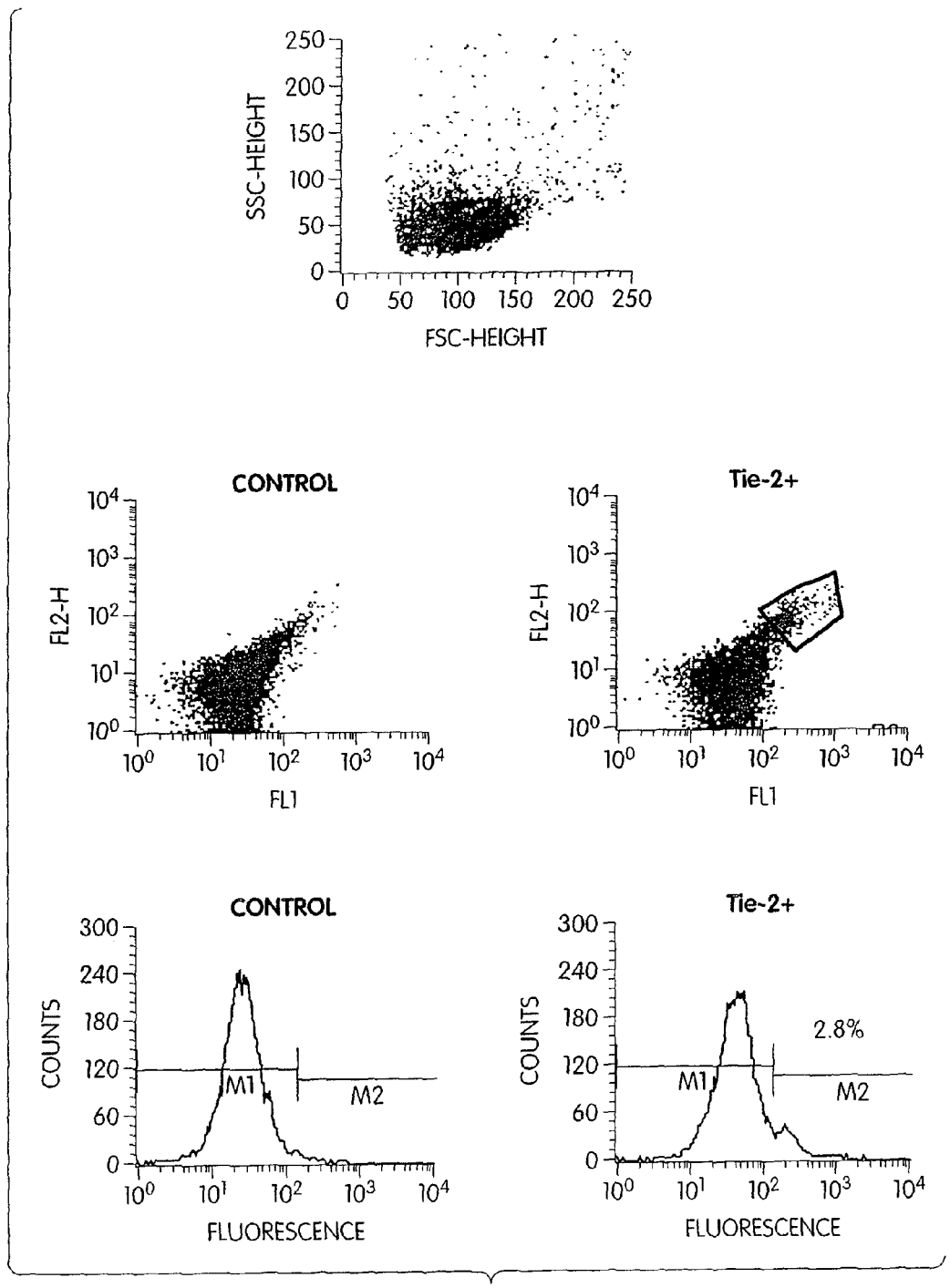
FIG. 1 shows dot plots representing forward and side scatter profile as well as fluorescence of peripheral blood mononuclear cells (PRMCs) stained with anti-Tie-2+ monoclonal antibodies (Mabs). Tie-2+ cells (grey dots) appeared in the lymphocyte gate. Histograms show the percentage of Tie2+ cells (app. 2±3%) in PBMCs stained with negative control abs and Tie-2-Mabs.

The invention is based in part on the discovery that targeting a single specific cell population allows for the detection of clinically relevant donor-specific human leukocyte antigens (HLA) class I, class II, endothelial-monocytes, or endothelial cell-specific antibodies prior to transplantation of organs. Routine use of the endothelial cell cross matching will aid in identifying better donor-recipient combinations and thus have a greater impact on transplant survival as compared to traditional lymphocyte cross matching.

The clinical importance of endothelial cell (EC) antibodies in allo-transplantation has been reported. However, lack of a suitable method for isolation of donor-specific ECs has prevented routine detection of these antibodies prior to transplantation. The invention provides a quick and simple method for the direct isolation of ECs from whole blood, for routine cross-matching to detect anti-EC antibodies. The presence of endothelial cell-reactive antibodies has previously been detected using human umbilical vein endothelial cell (HUVEC) lines, keratinocyte cell lines, or monocytes as targets, or by immunohistochemistry. However, these methods are cumbersome because endothelial cell culturing is tedious and a generally large panel of donors of HUVEC lines/keratinocytes is required to represent all the known polymorphic alleles for screening of endothelial cell-reactive antibodies. Moreover, these methods do not permit the detection of donor-specific endothelial cell antibodies. Thus, use of an endothelial cell cross-match is advantageous over use of lymphocyte cross-match because lymphocyte cross-match does not allow for such detection or isolation of donor-specific endothelial cell-reactive antibodies.

ECs were isolated using magnetic beads coated with antibodies against the angiopoietin receptor, Tie-2 that is expressed on EC precursors. Tie genes play an important role in renal vascular development, and based on transplantation experiments these precursors have been shown to contribute to the generation of glomerular maturation. A retrospective analysis of 50 previously well characterized crossmatch sera taken immediately prior to transplantation from patients with end-stage kidney disease were tested. Tie-2+ cells expressed HLA class I, class II and other endothelial cell markers. Sera known to contain only EC specific or EC and monocyte (EM) reactive antibodies reacted positively with Tie-2+ cells, but not with Tie-2– cells from the same individual. In addition, the Tie-2+ cells reacted with sera containing only HLA class I or class II abs. In all, 3/25 sera from patients with stable graft outcome and no rejections reacted with Tie-2+ cells. This antigen-antibody interaction is relevant to the pathogenesis of rejection, since in many studies these antibodies are not detected in the serum of patients with good graft function or in non-transplantation patients.

Methods of Isolating Endothelial Cells

The invention includes methods of isolating an endothelial cell from a mixture of cells by contacting the mixture of cells with a detection reagent to form a endothelial cell-detection reagent complex. The complex is formed via a specific affinity interaction between the detection reagent and the cell. The complex is separated from the mixture to isolate the endothelial cell. The complex is separated from the mixture using techniques known in the art, such as by, e.g., liquid chromatography (e.g., HPLC or FPLC), High Performance Membrane Chromatography (HPMC), flow cytometry or use of a magnetic field. Alternatively, the complex is separated from the mixture by attaching the detection reagent to a solid support. A washing step may be employed by re-suspending the complex in a biologically compatible solution. The complex can be re-suspended, i.e., washed as many times as desired. Typically the particles are washed three times. A biologically compatible solution include biological buffers known in the art such as phosphate buffer saline (PBS).

The detection reagent is an endothelial cell detection reagent. An endothelial cell detection reagent is any reagent that specifically identifies an endothelial cell. For example, the detection reagent is a ligand for a endothelial cell surface receptor. The endothelial cell surface receptors include, for example, the EC-specific tyrosine kinase receptor Tie-2 or VEGFR. The ligand is for example angiopoietin, VEGF or an antibody specific for the cell surface receptor. The antibody is a monoclonal antibody or a polyclonal antibody. The term antibody encompasses not only an intact antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin. For example the detection reagent is monoclonal antibody Tie-2 or VEGFR-1

The detection reagent is attached to a solid support. The solid support is a particle, a polymer (e.g., polystyrene, polyethylene), a vessel, a chamber, a dipstick, beads, particles, membranes (e.g., nylon, nitrocellulose or polyvinylidenedifluoride (PVDF)), or other forms known in the art.

The solid support may carry functional groups such as hydroxyl, carboxyl, aldehyde or amino groups. The solid support may be positively charged, negatively charged or hydrophobic. Functionalized coated supports for use in the present invention may be prepared by modification of the support. For example, uncoated support is treated with a polymer carrying one or such functional groups, such as polyurethane together with a polyglycol to provide hydroxyl groups, or a cellulose derivative to provide hydroxyl groups, a polymer or copolymer of acrylic acid or methacrylic acid to provide carboxyl groups, or an aminoalkylated polymer to provide amino groups. U.S. Pat. No. 4,654,267 describes the introduction of many surface coatings.

The particle is made of metal compounds, silica, latex, polymeric material, or a silica, latex or polymer nuclei coated with a metal or metal compound. Preferably, the particle is made of a metal compound, such as iron, gadolinium, zinc, indium, gold, silver, cobalt, copper, or magnesium. Most preferably, the particle is magnetizable or magnetic. By "magnetizable or magnetic" is meant that the particle is capable of having a magnetic moment impaired to it when it is placed in a magnetic field.

The detection reagent is labeled with a detectable marker. For example the detection reagent to labeled with a radioactive isotopes (e.g., $^{125}I$, and $^{131}I$), enzymes (e.g., peroxidase, beta.-galactosidase, alkaline phosphatase) or fluorescent substances (e.g., fluorescein isothiocyanate (FITC). The labels are quantified by the conventional methods well-known in the art, thereby the formed immune complex is quantified. The mixture of cells is any sample known to or suspected of containing an endothelial cell. For example the mixture is a biological sample such as whole blood, sera, leucapherisate, bone marrow, peripheral blood mononuclear cells or a tissue homogenate.

An endothelial cell is any cell derived from any part of the vascular tree. For example the endothelial cell is from large and small veins and arteries capillaries, the umbilical vein of newborns, blood vessels in the brain or from vascularized solid tumors. The endothelial cell is a mature cell. Alternatively, the endothelial cell endothelial cell precursor. Preferably, the endothelial cell is Tie-2 positive.

Methods of Donor Specific Crossmatching

Cross-matching detects those antigenic differences to which the recipient is already sensitized. A donor is cross-matched to a recipient by contacting a donor sample with a detection reagent to isolate an endothelial cell. The recipient sample is contacted with the isolated endothelial cell and reactivity of the recipient sample with the isolated endothelial cell is determined. By "reactivity" it is meant that that a complex is formed via a specific affinity interaction between the recipient sample and the cell. No reactivity of the recipient sample with the isolated endothelial cell indicates compatibility between the donor and recipient sample. In contrast, reactivity of the of the recipient sample with the isolated endothelial cell indicates non-compatibility between the donor and recipient sample. Compatibility is measured by no or low hyperacute rejection of the donor transplant by the recipient.

The donor and the recipient are, e.g., any mammal, e.g., a human, a pig, a cow, or a horse. The donor and the recipient are the same species. Alternatively, the donor and the recipient are of different species.

The donor and recipient sample is, for example, whole blood, sera, leucapherisate, bone marrow, peripheral blood mononuclear cells or a tissue homogenate. Optionally, the samples are subjected to a pre-purification step prior to cross-matching.

Reactivity is determined my methods known in the art. For example reactivity is measured by an ELISA assay, flow cytometry (e.g. flow cytometric cross-match), or complement-dependent lymphotoxicity cross-match.

Vascular and Immune Disorders

The invention also provides methods of diagnosing, accessing the prognosis or monitoring the course of treatment of vascular and immune disorders.

In these methods a first test sample is provided from a subject The sample is known to or suspected of containing an endothelial cell. Optionally, the endothelial cell is isolated from the first sample.

An immune disorder is diagnosed by contacting the first sample to a second sample from the subject known to contain, or suspected of containing, an auto-antibody and identifying an autoantibody-endothelial cell complex. The presence of an autoantibody-endothelial cell complex indicates the subject is suffering from or predisposed to an immune disorder. In contrast, the absence of an autoantibody-endothelial cell complex indicates the subject is not suffering from or predisposed to an immune disorder.

A vascular disorder is diagnosed by contacting the first sample to a second sample. The second sample is derived from the subject. Alternatively, the second sample comprises antibodies to cell surface markers know to be associated with a particular vascular disorder The presence of a second sample-endothelial cell complex indicates the subject is suffering from or predisposed to a vascular disorder. In contrast, the absence of a second sample-endothelial cell complex indicates the subject is not suffering from or predisposed to a vascular disorder.

The methods allow the course of treatment of a vascular or immune to be monitored or the prognosis of the subject to be determined. In this method, a test sample is provided from a subject undergoing treatment for the disorder. If desired, test samples are obtained from the subject at various time points before, during, or after treatment. The presence of an endothelial cell complex is then determined to create a subject profile. The subject profile is compared to a reference profile whose vascular disorder or immune disorder state is known. The reference profile has not been exposed to the treatment. The reference profile is derived from a sample type as similar to test sample. Optionally, the reference profile is derived from a database of molecular information derived from samples for which the assayed parameter or condition is known.

If the reference profile contains no autoantibody-endothelial cell complexes, a similarity in the amount of complexes between the subject profile and the reference profile indicates that the treatment is efficacious (e.g., that one or more symptoms of the immune disorder are alleviated or that the severity of the disorder is reduced), and thus, a favorable prognosis for the subject. However, a shift in the amount of complexes between the subject profile and the reference profile indicates that the treatment is not efficacious, and thus, an unfavorable prognosis for the subject.

When the reference profile contains autoantibody-endothelial cell complexes, e.g., when the reference profile includes complexes taken from the subject at the time of diagnosis but prior to beginning treatment, a similarity in the expression of complexes pattern between the subject profile and the reference profile indicates the treatment is not efficacious. In contrast, a shift in expression complexes in the subject profile and this reference profile indicates the treatment is efficacious.

By "efficacious" it is meant that the treatment leads to a decrease in any of the symptoms of an autoimmune disorder in a subject previously noted. When treatment is applied prophylactically, "efficacious" means that the treatment retards or prevents an immune related or vascular disorder.

An immune disorder includes disorders mediated by an immune mechanism such as deposition of immune complexes, inflammation, direct attack by circulating antibodies (e.g., autoimmune disorders). An autoimmune disorder or an autoimmune related disorder includes those disorders caused by an immune response against the body's own tissues. Autoimmune disorders result in destruction of one or more types of body tissues, abnormal growth of an organ, or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints, and skin. Autoimmune disorders include for example, autoimmune hemolytic anemia, autoimmune hepatitis, Berger's disease, chronic fatigue syndrome, Crohn's disease, Hashimoto's thyroiditis, fibromyalgia, systemic lupus erthyematosus, Graves' disease, idiopathic thrombocytopenia purpura, multiple sclerosis, psoriasis, rheumatic fever, rheumatoid arthritis, Vascular disorders include disease associated with the vascular system. For example vasculitis, atherosclerosis, bleeding disorders, defective wound healing.

Symptoms of an autoimmune disorder depend on the specific disease and the organ or tissue that is affected. For example, systemic lupus erythematosus may cause kidney failure, arthritis, and a skin rash on the face. Autoimmune hemolytic anemia causes anemia, or low red blood cell counts. Generally symptoms of autoimmune disorders may include: low-grade fever, malaise, which is a vague feeling of illness, fatigue, or tiring easily. Autoimmune disorders are diagnosed based on symptoms, a physical exam, and the results of blood tests.

Treatments to reduce symptoms may include: nonsteroidal anti-inflammatory drugs (NSAIDs), including aspirin or ibuprofen, to relieve fever, joint pain, and muscle aches corticosteroids, or steroids, help reduce inflammation. These medications are often used on a short-term basis to get a person through a sudden episode or flare-up, medications to suppress the immune system, such as methotrexate, azathioprine, and cyclophosphamide, which help to reduce inflammation and organ damage. In some cases, other treatments may be needed. For example, surgery may be needed for blockage of the bowels, which may occur in Crohn's disease. Blood transfusions may be needed in severe cases of autoimmune hemolytic anemia. Insulin is given to individuals with type 1 diabetes to control blood glucose levels.

The subject is preferably a mammal. The mammal can be, e.g., a human, non-human primate, mouse, rat, dog, cat, horse, or cow.

General Methods

The data described herein was generated using the following reagents and methods.

Example 1

Coupling of anti-Tie-2 Mabs to Magnetic Beads

Mouse anti-human Tie-2 monoclonal abs. (Mabs) (BD Pharmingen, Oxford, UK) were first coupled to pan-mouse Dynabeads with a DNA-linker (cat. no. 115.19)(DYNAL, Oslo, Norway). For this purpose, 10 μg of Tie-2 Mabs were added to 500 μls of pan-mouse Dynabeads. The bead-Mab suspension was rotated on a rock n' roller for 24 hrs at 4° C. Excess Mab was removed and the Tie-2 Mab coated beads were blocked with 2 ml phosphate buffered saline (PBS) containing 0.1% bovine serum albumin (BSA) on a rock n' roller at 4° C. for 10 min. The blocking step was repeated six times after which, the beads were resuspended in original volume (500 μls) of PBS/0.1% BSA.

Example 2

Isolation of Tie-2+ Cells from Peripheral Blood Mononuclear Cells (PBMC)

Due to the large numbers of cells required to establish the specificity of the Tie-2+ cells, in the initial experiments PBMCs were isolated from leucapherisate of healthy blood donors by gradient centrifugation with lymphoprep (Nycomed-Oslo, Norway). ECs were isolated from PBMCs using anti-Tie-2 Mabs coated magnetic beads. PBMCs were first distributed into several tubes each containing $40 \times 10^6$ cells. Fifteen μls of pre-coated Tie-2 magnetic beads were added to each tube and incubated in a volume of 500 μls RPMI medium (GIBCO, Paisley, UK) supplemented with 2 mM L-glutamine and 10% heat inactivated fetal calf serum. Cells+ beads were incubated on rock 'n roller at 4° C. for 30 min. Tie-2+ cells were separated after extensive washing (5-6 times) with PBS using a magnet. Tie-2+ cells from all tubes were pooled together and rosettes were counted under a light microscope.

Example 3

Isolation of Tie-2+ Cells Directly From Peripheral Blood 40 ml-heparinized blood was obtained from normal healthy donors. The blood was washed once as follows: 10 ml blood was diluted with 40 ml PBS/0.1% BSA. The blood was centrifuged at 800 g for 10 min. The supernatant was discarded and the blood cells were resuspended in 10 ml of PBS containing 0.6% sodium citrate. Fifty μls of Tie-2 Mabs coated magnetic beads were added to each tube and incubated for 30 min at 4° C. on a rock 'n roller. Tie-2+ cells were collected by a magnet and washed once with PBS-Na-citrate. After 4-5 washes with PBS, Tie-2+ cells were collected and the concentration of the cells adjusted to approximately $3-4 \times 10^6$ cells/ml. These cells surrounded by beads were used either in a microcytotoxicity assay or the flow cytometer.

Example 4

Immunocytochemistry

The Mabs used for immunocytochemistry and FACs analysis are given in Table 1. Tie-2+ cells obtained from leucapherisate of normal volunteers gave sufficient numbers of cells to perform various immunocytochemical analysis. Tie-2+ cells were grown on fibronectin-coated tissue culture plates. Cells were allowed to attach (24 hrs) prior to staining for various EC-specific markers. Cells were left either untreated or stimulated with TNF-α and IFN-γ for 14 hrs. For immunocytochemistry, cells were fixed using 30% acetone in methanol for 1 min. After two washes with PBS, cells were blocked using 1% bovine serum albumin (BSA) in PBS for 1 hr at room temperature. The cells were washed twice with PBS and incubated with the above mentioned primary antibodies diluted 1:100 (in PBS) at 4° C. for 2 hrs. The secondary antibody was a goat anti-mouse IgG conjugated with fluorescein isothiocyanate (FITC) diluted 1:500 (in PBS). After incubation for 1 hr at 4° C., the cells were washed twice and analysed under a fluorescence microscope.

Example 5

Flow Cytometric Assay for Detection of Anti-endothelial Cell Antibodies

A total of 50 sera from kidney-transplanted patients were studied. Over the past years (1988-2001) the pre-transplant sera from kidney patients has been meticulously characterized, using various methods, for the presence of endothelial cell specific, endothelial-monocyte reactive, and HLA antibodies found to be associated with rejections. During these years 15 pre-transplantation sera, characterized as having either anti-EM or EC specific antibodies from non-alloimmunized patients with rejections, have been collected.

The general methods described herein are based on these 15 sera. Previous characterization showed that ten sera gave positive reactions with human umbilical vein endothelial cell (HUVECs) lines and monocytes (Table 2, pt. nos. 1-10), and five sera with only ECs (Table 2, pt. nos. 11-15). Since none of the fifteen patients with EM or EC-specific antibodies had been alloimmunized, no detectable HLA alloantibodies were found in these sera. In addition, ten well-characterized sera from alloimmunized patients known to contain only HLA class I or only class II alloantibodies were selected (Table 2). As controls, 25 sera from patients with no graft rejections were also tested.

Using these sera, it was determined whether the isolated Tie-2+ cells could be suitable targets for detection of clinically relevant antibodies in kidney organ transplantation. A pool of sera from patients who had formed alloantibodies as a result of multiple blood transfusions or organ transplantations was used as a positive control. Sera from healthy non-transfused blood group AB males served as negative controls. The following antibodies, FITC-conjugated F(ab')$_2$ fragments of goat anti-human IgG (Fc specific), or IgM (Immunotech, USA) were used. For the flow cytometric ECXM 100,000 Tie-2+ cells coupled to beads were used and the procedure carried out as described earlier. The cells were analyzed on a Becton Dickinson flow cytometer (FACSorter). A shift in the mean fluorescence of 10 channels in the test sample as compared to negative control was considered as positive, determined as described before. This value is arbitrary and should be determined by each transplant laboratory. The Tie-2+ cells were also used in the routinely performed immuno-magnetic microcytotoxicity assay as described elsewhere. In addition, Tie-2+ cells immediately after isolation were tested in the flow cytometer for all the endothelial cell surface markers (Table 1).

Example 6

Figure 2A:
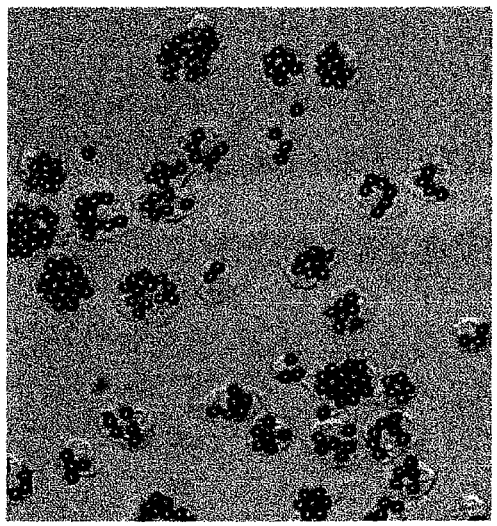
FIGS. 2a-c are photographs of the morphology of Tie-2+ cells under light microscope at various time points after isolation from peripheral blood. Initially, these cells appeared either as single cells or as clusters of round cells (a), which after few days of culture converted into adherent cells with extended cytoplasm, (the dark objects are beads) (b). After 7-12 days in culture the cells gradually developed a spindle shape (c).
Figure 2B:
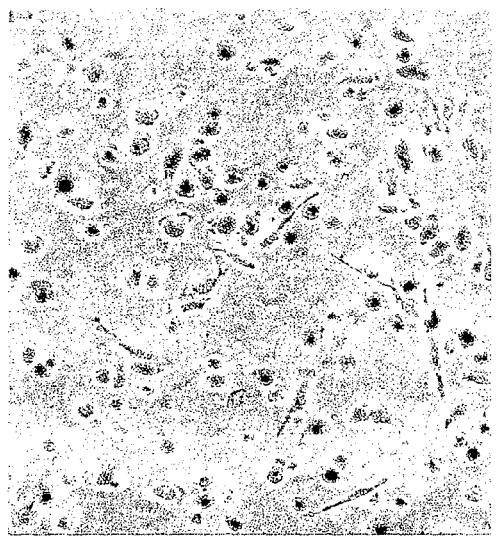
Figure 2C:
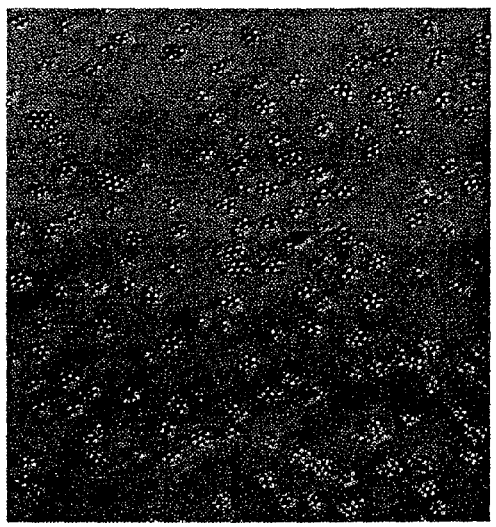
Figure 3A:
FIG. 3a is a series of photographs showing Tie-2+ cells stained positive for the endothelial associated markers, acetylated low density lipoprotein (Ac-LDL), von Willebrand factor (vWF), vascular endothelial growth factor receptor-1 (VEGFR-1) and the vascular cell adhesion molecule (VCAM)(on activated Tie-2+ cells). Tie-2+ cells also constitutively expressed the human leukocyte antigen class I (HLA class I) and the monocyte/macrophage marker CD68.
Figure 3A:
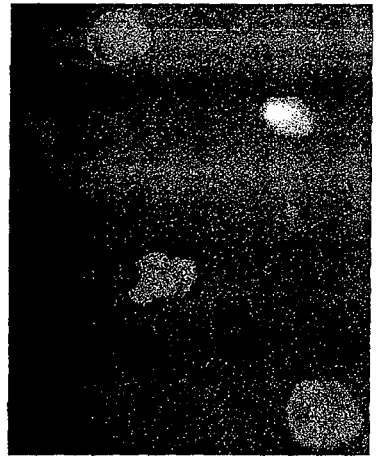
Figure 3A:
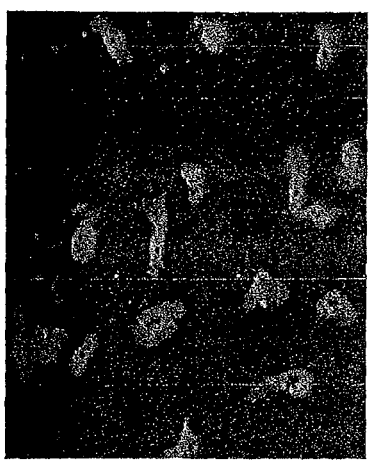
Figure 3A:
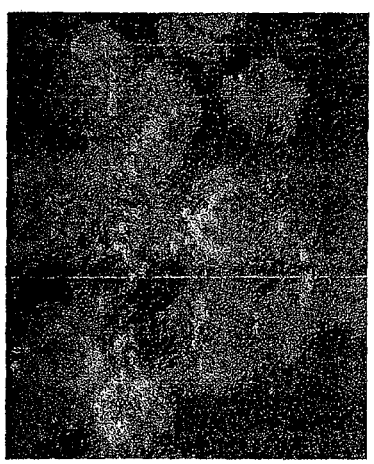
Figure 3A:
Figure 3A:
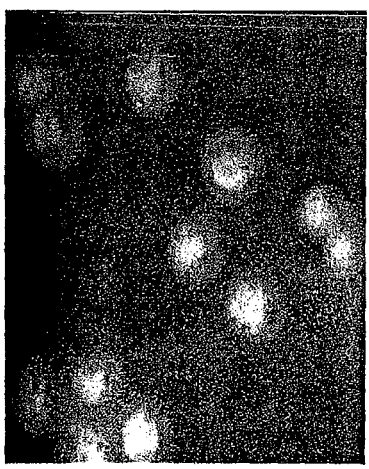
Figure 3B:
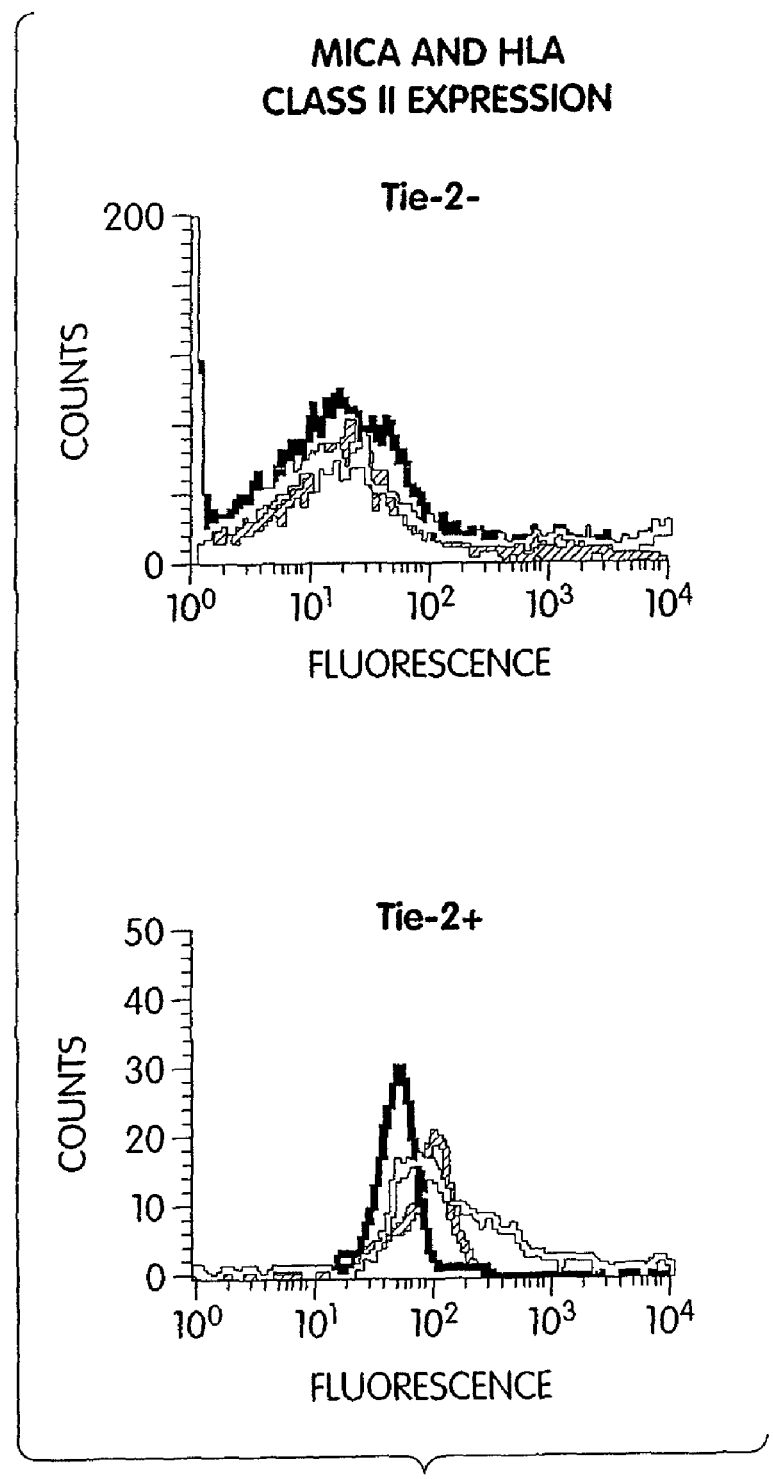
FIG. 3b shows that quiescent Tie-2+ cells expressed small amounts of the clinically important MICA antigens (dark grey), and HLA class II (light grey), control antibodies (black).

Immunocytochemistry and FACS Analysis of Endothelial Cell Markers on Isolated Tie-2+ Cells Tie-2+ ECs were isolated from human peripheral blood by magnetic bead selection. FACS analysis showed that approximately 3±4% of PBMCs were Tie-2+ (FIG. 1). After 24 hours in culture, the majority of Tie-2+ cells attached to fibronectin-coated 24 well plates and became adherent. Initially, these cells appeared either as single cells or as clusters of round cells, which after few days of culture converted into adherent cells with extended cytoplasm. After 4 days in culture the cells gradually developed spindle shape (FIGS. 2a-c).

FIG. 3 and Table 1 summarize the results of the immunocytochemical analyses using antibodies to known antigens of endothelial cells. Already at 0 hours, FACS analysis indicated that Tie-2+ cells expressed the acLDL-receptor, vWF, VEGFR-1, and strong expression of HLA class I and HLA class II antigens. Importantly, the cells expressed the clinically important MICA antigen, though weakly. Upon cytokine activation, the cells expressed both the endothelial cell specific adhesion molecules CD62 E (E-selectin) and CD 106 (VCAM), as well as increased expression of HLA class II. Thus, both the immunocytochemical and FACS analysis indicated that Tie-2+ cells expressed majority of the endothelial cell markers.

Example 7

Detection of Anti-endothelial Cell Reactive Antibodies

On an average, approximately, $3\pm4\times10^4$ Tie-2+ cells/$10^6$ PBMCs can be obtained from single donors. Since a large number of sera were analyzed herein Tie-2+ cells from leucapherisate of healthy blood donors were isolated. The results are shown in Table 2. All the 10 sera known to have endothelial-monocyte antibodies and 5 sera with endothelial cell-specific antibodies showed varying patterns of reactivity with the panel of Tie-2+ cells from six different donors. However, the Tie-2− fractions, which included the lymphocytes from the same donors, did not react with any of the sera. The reactivity pattern with the Tie-2+ cell panel of both the endothelial-monocyte and endothelial cell-specific antibodies as seen in Table 2, indicates the existence of polymorphism in these antigenic systems or alternatively presence of antibodies with varied specificities.

Sera known to contain only HLA class I broadly reactive alloantibodies also gave positive reactions in every instance with Tie-2+ cells from single donors. Reactivity of HLA class II alloantibodies (limited specificities) was also observed with unstimulated Tie-2+ cells. 3/25 (12%) sera from control patients with no rejections and with stable graft functions gave positive reactions with four of the Tie-2 panel donors (Table 2). Results obtained using the immuno-magnetic microcytotoxicity assay were in agreement with the flow cytometric analysis (Table 3).

Example 8

Donor-specific Endothelial Cell Cross-match

Donor-specific endothelial cell crossmatches were retrospectively performed in two cases where frozen donor peripheral blood mononuclear cells were available. The first kidney grafts of both patients were lost in hyperacute rejections in the absence of demonstrable donor-specific HLA antibodies. Cross-match sera from one of these patients had been previously well characterized as having anti-endothelial cell-specific antibodies using HUVECs.

Figure 4A:
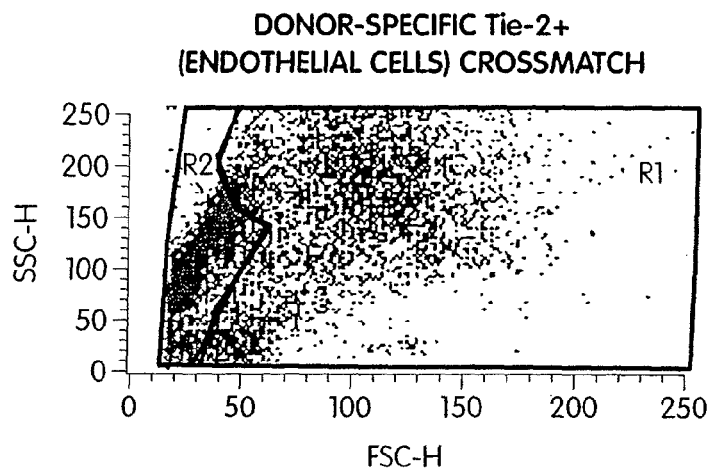
FIG. 4a is a dot plot that represents the forward and side scatter of rosettes of Tie-2+ cells and paramagnetic beads (gate R1) and paramagnetic beads only (gate R2).
Figure 4B:
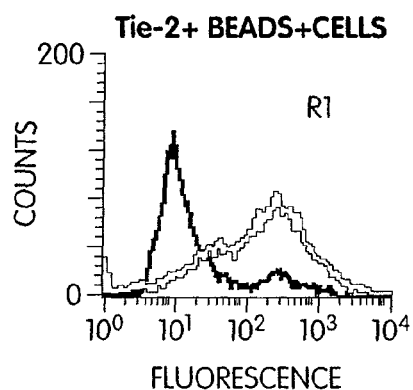
FIGS. 4b-g are histograms showing that pre-transplant sera from two kidney-transplanted patients with hyperacute rejections reacted strongly with their respective donor-specific Tie-2+ cells (b & e), while their Tie-2– fractions, which included lymphocytes did not (d & g). Histograms c & f show that the paramagnetic beads alone did not react with the sera non-specifically. The grey lines represent control or negative sera, and the black lines represent reactivity with patient's sera.
Figure 4C:
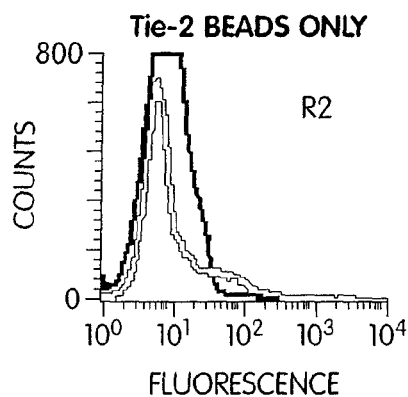
Figure 4D:
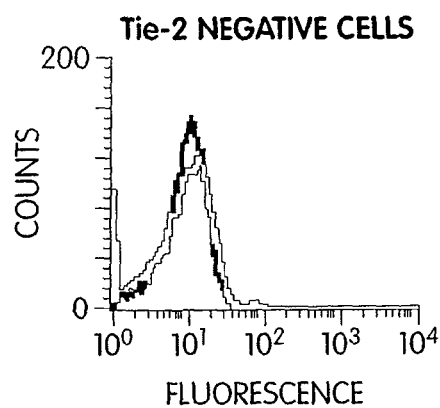
Figure 4E:
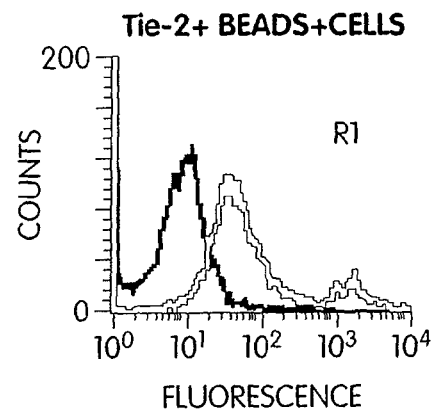
Figure 4F:
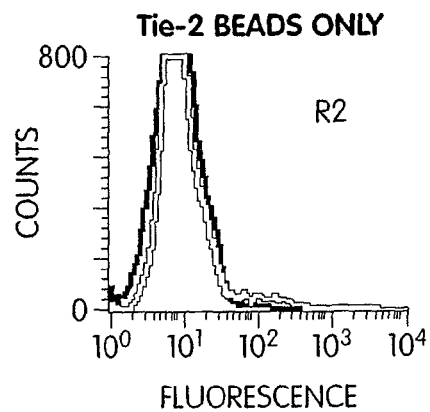
Figure 4G:
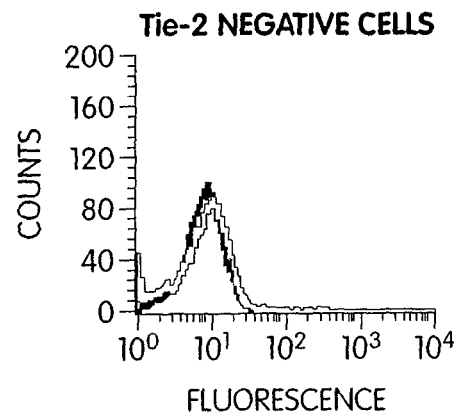

In this instance, Tie-2+ cells from the peripheral blood mononuclear cells of this patient's (point. no. 11, Table 2) first donor (father) were isolated and kept frozen in liquid $N_2$. A cross-match with the serum of the patient taken immediately prior to the first transplant was retrospectively performed. The results are shown in FIGS. 4b-d. The results from a second case (point. no. 12, Table 2) are very similar to point no. 11, and are shown in FIGS. 4e-g. As seen, in Table 2, the sera from both these points gave similar pattern of reactivity with Tie-2+ cell panel. No reactivity with the Tie-2− fractions were observed.

TABLE 1

Antibodies used in immunocytochemical staining and flow cytometric analysis of Tie-2+ cells isolated from whole blood

| Antibodies | Company | Immuno-cytochemistry | FACS |
|---|---|---|---|
| CD1a | Becton Dickinson (BD)-USA | − | − |
| CD3 | BD | − | − |
| CD14 | BD | (+)/+ | (+)/+ |
| CD19 | BD | − | − |
| CD31 | BD | − | − |
| CD34 | BD | − | − |
| CD56 + 16 | BD | − | − |
| CD68 | BD | ++ | ++ |
| CD83 | BD | − | − |
| CD62E (anti-E-selectin) | Biogenesis-UK | +* | +* |
| CD106 (anti-VCAM) | Biogenesis-UK | ++* | ++* |
| CD54 (anti-ICAM) | R&D Systems-UK | +* | +* |
| VWF | SEROTEC-UK | ++ | ++ |
| Ac-LDL | Molecular Probes, Inc-USA | +++ | +++ |
| VEGF-R1 (Flt-1) | R&D Systems | +++ | +++ |
| MHC class I | Serotec-UK | +++ | +++ |
| MHC class II | Serotec-UK | + | ++ |
| MICA | Dr. Thomas Spies | (+)/+ | (+)/+ |
| Anti-Fibroblast | Serotec-UK | − | − |
| Anti-α-actin | Boehringer Mannheim-Germany | − | − |

(+), weak or inconsistent staining; +, moderate staining; ++, strong staining; +++, very strong staining. vWF, vonWillebrand Factor; Ac-LDL, acetylated low-density lipoprotein; MICA, Major histocompatibility complex class I- related chain A.
*expressed on Tie-2+ cells only after activation with TNF-alpha and IFN-gamma for 12-14 hrs.

TABLE 2

Flow cytometric analysis of reactivity of anti-endothelial-monocyte, endothelial specific and HLA class I or class II specific antibodies with a panel of Tie-2+ cells

| Pt. No. | Donor 1 Tie-2+/Tie2− | Donor 2 Tie2+/Tie2− | Donor 3 Tie2+/Tie2− | Donor 4 Tie2+/Tie2− | Donor 5 Tie2+/Tie2− | Donor 6 Tie2+/Tie2− |
|---|---|---|---|---|---|---|
| Sera known to contain EM-reactive abs. | | | | | | |
| 1 | +/− | +/− | +/− | +/− | +/− | +/− |
| 2 | +/− | +/− | +/− | +/− | +/− | +/− |
| 3 | +/− | +/− | +/− | +/− | +/− | +/− |
| 4 | +/− | −/− | −/− | +/− | −/− | +/− |
| 5 | −/− | +/− | +/− | +/− | +/− | −/− |
| 6 | −/− | +/− | +/− | +/− | +/− | −/− |
| 7 | −/− | +/− | +/− | +/− | +/− | −/− |
| 8 | −/− | −/− | −/− | +/− | −/− | +/− |
| 9 | +/− | +/− | −/− | −/− | +/− | −/− |
| 10 | +/− | +/− | −/− | −/− | +/− | −/− |
| Sera known to contain only EC-specific abs. | | | | | | |
| 11 | +/− | +/− | −/− | +/− | −/− | −/− |
| 12 | +/− | +/− | −/− | +/− | −/− | −/− |
| 13 | −/− | −/− | +/− | −/− | +/− | +/− |
| 14 | −/− | −/− | +/− | −/− | +/− | +/− |
| 15 | −/− | −/− | +/− | −/− | +/− | +/− |
| Sera known to contain only HLA class I broadly-reactive abs. (n = 5) | | | | | | |
| 16 | +/+ | +/+ | +/+ | +/+ | +/+ | +/+ |
| Sera known to contain only HLA class II abs. (n = 5) | | | | | | |
| 17 | +/+ | −/− | −/− | +/+ | −/− | +/+ |
| Control sera from pts. with stable graft function (n = 25) | | | | | | |
| 18 | −/−* | −/− | −/−* | −/− | −/− | −/−* |

*3/25 (12%) sera reacted with some of the Tie-2 cells on the panel

TABLE 3

Reactivity of anti-endothelial-monocyte, endothelial specific and HLA class I or class II specific antibodies with a panel of Tie-2+ cells using the microcytotoxic assay

| Pt. No. | Donor 1 Tie-2+/Tie2− | Donor 2 Tie2+/Tie2− | Donor 3 Tie2+/Tie2− | Donor 4 Tie2+/Tie2− | Donor 5 Tie2+/Tie2− | Donor 6 Tie2+/Tie2− |
|---|---|---|---|---|---|---|
| Sera known to contain EM-reactive abs. | | | | | | |
| 1 | ++/− | +++/− | ++/− | ++/− | ++/− | +++/− |
| 2 | ++/− | +/− | +++/− | ++/− | +++/− | ++/− |
| 3 | +++/− | ++/− | ++/− | ++/− | ++/− | ++/− |
| 4 | +++/− | −/− | −/− | +++/− | −/− | +++/− |

TABLE 3-continued

Reactivity of anti-endothelial-monocyte, endothelial specific and HLA class I or class II specific antibodies with a panel of Tie-2+ cells using the microcytotoxic assay

| Pt. No. | Donor 1 Tie-2+/Tie2− | Donor 2 Tie2+/Tie2− | Donor 3 Tie2+/Tie2− | Donor 4 Tie2+/Tie2− | Donor 5 Tie2+/Tie2− | Donor 6 Tie2+/Tie2− |
|---|---|---|---|---|---|---|
| 5 | −/− | ++/− | ++/− | ++/− | ++/− | −/− |
| 6 | −/− | ++/− | ++/− | ++/− | ++/− | −/− |
| 7 | −/− | ++/− | ++/− | ++/− | ++/− | −/− |
| 8 | −/− | −/− | −/− | ++/− | −/− | ++/− |
| 9 | +++/− | ++/− | −/− | −/− | ++/− | −/− |
| 10 | ++/− | ++/− | −/− | −/− | ++/− | −/− |
| Sera known to contain only EC-specific abs. | | | | | | |
| 11 | +++/− | ++/− | −/− | +++/− | −/− | −/− |
| 12 | ++/− | +++/− | −/− | ++/− | −/− | −/− |
| 13 | −/− | −/− | ++/− | −/− | ++/− | ++/− |
| 14 | −/− | −/− | ++/− | −/− | ++/− | ++/− |
| 15 | −/− | −/− | ++/− | −/− | ++/− | ++/− |
| Sera known to contain only HLA class I broadly-reactive abs. (n = 5) | | | | | | |
| 16 | +++/+++ | +++/+++ | ++++/++++ | +++/+++ | +++/+++ | ++/++ |
| Sera known to contain only HLA class II abs. (n = 5) | | | | | | |
| 17 | ++/++ | −/− | −/− | ++/++ | −/− | ++/++ |
| Control sera from pts. with stable graft function (n = 25) | | | | | | |
| 18 | −/−* | −/− | −/−* | −/− | −/− | −/− |

*2/25 (8%) sera reacted with some of the Tie-2 cells on the panel
−, negative; +, 10-25%; ++, 26-50%; +++, 51-75%; +++, 76-100% dead cells.

REFERENCES

Kissmeyer-Nielsen F, Olsen S, Posborg-Petersen V, Fjeldborg O. Hyperacute rejection of kidney allografts, associated with pre-existing humoral antibodies against donor cells. *Lancet* 1966; 2: 662.

Ting A. Positive crossmatches—when is it safe to transplant? *Transplant Int.* 1989; 2:2.

Sumitran-Karuppan S. The clinical importance of choosing the right assay for detection of HLA-specific donor-reactive antibodies. *Transplantation* 1999; 68: 502.

Chapman J R, Taylor C J, Ting A, Morris P J. Immunoglobulin class and specificity of antibodies causing positive T cell crossmatches. Relationship to renal transplant outcome. *Transplantation* 1989; 42: 608.

Brasile L, Rodman E, Shield C F d, Clarke J, Cerilli J. The association of antivascular endothelial cell antibody with hyperacute rejection: a case report. *Surgery* 1986; 99:637.

Sumitran-Karuppan S, Tyden G, Reinholt F, Berg U, Moller E. Hyperacute rejections of two consecutive renal allografts and early loss of the third transplant caused by non-HLA antibodies specific for endothelial cells. *Transplant Lmmunol.* 1997; 5: 321.

Cerilli J, Brasile L. Endothelial cell alloantigens. *Transplant. Proc.* 1980; 12 (3 Suppl 1): 37.

Stastny P. Endothelial-monocyte antigens. *Transplant. Proc.* 1980; 12 (3 Suppl 1): 32.

Pierce J C, Waller M, Phibbs M. A mixed antiglobulin test with kidney cells in suspension for IgG antibody in human allograft recipients. *Transplantation* 1975; 19: 343.

Wilson C B. Individual and strain differences in renal basement membrane antigens. *Transplant. Proc.* 1980; 12 (3 Suppl 1): 69.

Paul L C, Carpenter C B. Antibodies against renal endothelial alloantigens. *Transplant. Proc.* 1980; 12 (3 Suppl 1): 43.

Mohanakumar T, Waldrep J C, Phibbs M, Mendez-Picon G, Kaplan A M, Lee H M. Serological characterization of antibodies eluted from chronically rejected human renal allografts. *Transplantation* 1981; 32: 61.

Hosenpud J D, Everett J P, Morris T E, Mauck K A, Shipley G D, Wagner C R. Cardiac allograft vasculopathy. Association with cell-mediated but not humoral alloimmunity to donor-specific vascular endothelium. *Circulation* 1995; 92: 205.

Perrey C, Brenchley P E, Johnson R W, Martin S. An association between antibodies specific for endothelial cells and renal transplant failure. *Transplant Immunol.* 1998; 6: 101.

Kalil J, Guilherme L, Neumann J, et al. Humoral rejection in two HLA identical living related donor kidney transplants. *Transplant. Proc.* 1989; 21 (1 Pt 1): 711.

Sumitran-Holgersson S, Wilczeck H, Holgersson J and Soderstrom K: Identification of the non-classical HLA molecules, MICA, as targets for humoral immunity associated with irreversible rejections of kidney allografts. Accepted. *Transplantation.*

Cerilli J, Bay W, Brasile L: The significance of the monocyte crossmatch in recipients of living-related HLA identical kidney graft. *Hum Immunol.* 1983; 7: 45.

Ianhez L, Saldanha L B, Paula F J et al: Humoral rejection with negative crossmatches. *Transplant Proc.* 1989; 21: 720.

Asahara T, Murohara T, Sullivan A. Isolation of putative progenitor endothelial cells for angiogenesis. *Science* 1997; 275: 964.

Peichev M, Naiyer A J, Pereira D et al. Expression of VEGFR-2 and AC133 by circulating human CD34+ cells identifies a population of functional endothelial precursors. *Blood* 2000; 95: 952.

Vartdal F, Gaudernack G, Funderud S, Brattie A, Lea T, Ugerstad S and Thorsby E: HLA class I and II typing using cells positively selected from blood by immunomagnetic isolation—a fast and reliable technique. *Tissue Antigens* 1986; 28: 301.

Sumitran-Karuppan S, Lindholm A, Möller E: Fewer acute rejection episodes and improved outcome in kidney transplanted patients with changed selection of criteria based on cross-matching? *Transplantation* 1992; 53: 666.

Sumitran-Karuppan S, Moller E: Specific inhibition of HLA class I and II antibodies by soluble antigens—A method for the identification of antibody specificity in sera from alloimmunized individuals. *Transplantation* 1994; 58: 713.

Sumitran-Karuppan S, Moller E. The use of magnetic beads coated with soluble HLA class I or class II proteins in antibody screening and for specificity determinations of donorreactive antibodies. *Transplantation* 1996; 61: 1539.

Moraes J R, Moraes M E, Luo Y, Stastny P: Alloantibodies against donor epidermis and early kidney transplant rejection. *Transplantation* 1991; 51: 370.

Schnurch H, Risau W. Expression of Tie-2, a member of a novel family of receptor tyrosine kinases, in the endothelial cell lineage. *Development* 1993; 119: 957.

Woolf A S, Yuan H T. Angiopoietin growth factors and Tie receptor tyrosine kinases in renal vascular development. *Pediatr Nephrol.* 2001; 16: 177.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of isolating a precursor endothelial cell from a biological sample comprising:
    (a) providing a sample of whole blood, peripheral blood mononuclear cells, or leucapherisate containing or suspected of containing a precursor endothelial cell;
    (b) contacting the sample with an antibody specific against Tie-2 endothelial cell surface receptor or an antigen binding fragment of said antibody under conditions where the precursor endothelial cell and Tie-2 specific antibody, or antigen binding fragment thereof, are capable of forming a complex to produce a Tie-2 antibody precursor endothelial cell complex, or a Tie-2 antibody antigen binding fragment precursor endothelial cell complex; wherein the antibody or antigen binding fragment thereof is attached to a solid support; and
    (c) separating said complex from the sample, thereby isolating said precursor endothelial cell from said biological sample
    wherein the isolated precursor endothelial cell is CD34 negative and CD14 positive.

2. The method of claim 1, wherein the solid support is a non-magnetic, magnetic or a paramagnetic bead.

3. The method of claim 1, wherein the antibody is a Fab fragment.

4. The method of claim 1, wherein said antibody specific against Tie-2 endothelial cell surface receptor is a mouse anti-human Tie-2 monoclonal antibody.

5. The method of claim 1, wherein said precursor endothelial cell is characterized as CD34 negative using an antibody specific against CD34.

* * * * *